United States Patent [19]

Scher

[11] Patent Number: 5,004,599

[45] Date of Patent: Apr. 2, 1991

[54] METHOD OF TREATING NAILS

[76] Inventor: Richard K. Scher, 913 Gardner Dr., P.O. Box P107, Bay Shore, N.Y. 11706

[21] Appl. No.: 332,354

[22] Filed: Mar. 31, 1989

[51] Int. Cl.$^5$ ............................................. A61K 7/04
[52] U.S. Cl. ..................................... 424/61; 514/725
[58] Field of Search ................. 424/61; 514/559, 560, 514/725

[56] References Cited

U.S. PATENT DOCUMENTS 4,603,146  7/1986  Kligman .............................. 514/559

Primary Examiner—Thurman K. Page
Assistant Examiner—Susan S. Rucker
Attorney, Agent, or Firm—Ladas & Parry

[57] ABSTRACT

A method of treating nail units of animals including humans in which a preparation containing tretinoin is topically applied to the nail to promote growth of the nail unit.

3 Claims, No Drawings

METHOD OF TREATING NAILS

THE FIELD OF THE INVENTION

The invention relates to a method of treating nail units including slowing their aging and promoting their growth.

BACKGROUND

The nail unit in humans is a cutaneous structure located on the distal aspect of the digits of the upper and lower extremities. It is present on the dorsal surface and overlies the distal phalanx. Animals have related structure analagous to nails made up predominantly of keratin and known as hoofs, claws or talons. The nail plate constituting the cosmetic component of the nail unit is manufactured, in humans, predominantly by the nail matrix by a process of keratinization and condensation of specialized epithelial cells.

The nail plate, hereafter referred to simply the "nail" is, in the case of animals, in contact with the environment and therefore is subject to a variety of trauma. These include physical and chemical insults which have a deleterious effect, thus making it desirable to improve their flexibility, reverse brittleness and thickness, improve strength and obviate photo damage. It is also advantageous to improve the cosmetic appearance, particularly for humans, and animals produced for show purposes.

Nail units are also susceptible to a number of infections and diseases, cutaneous and/or systemic, which may require removal (evulsion). Thus, an agent capable of enhancing growth in such situations is greatly desired and would be helpful in general usage. Up to the present, no effective scientific modality exists for influencing the growth rates of nails in humans or reversing photodamage and the aging process. Consequently, the art seeks a method which will satisfy the above needs and which would provide a significant advance in the field of medicine, cosmetics, and veterinary science.

SUMMARY OF THE INVENTION

An object of the invention is to provide a method of treating nail units of animals, including humans, which will satisfy the demands and needs as expressed above.

A further object of the invention is to provide a method for treating nail units which will promote nail growth in humans and animals and retard the effects of aging on the components of the nail unit.

In accordance with the above and further objects of the invention, the method comprises topically applying to the nail of an animal a preparation containing tretinoin.

The method comprises topically applying the composition containing tretinoin to the entire nail structure, particularly the region of the cuticle proximal the nail fold which overlies the growth center of the nail known as the matrix.

The tretinoin is present in the preparation in a varying concentration of between about 0.025 to 50% by weight. The tretinoin is present in a vehicle which may be aqueous or non-aqueous.

In further accordance with the invention, the preparation is applied in a regimen to promote growth of the nail and the regimen includes the periodic re-application of the preparation to the nail unit. The frequency of the reapplication depends upon the need to achieve the desired results. Generally, the tretinoin is formulated in a topical liquid, gel or cream containing a number of other inert ingredients.

DETAILED DESCRIPTION OF THE INVENTION

The invention provides a method for promoting nail growth, retarding photo and other aging, enhancing nail texture and flexibility, and improving cellular turnover. The method is accomplished by topical application of the preparation containing tretinoin on the components of the nail unit.

The active component of the topical preparation is tretinoin which chemically is all-trans-retinoic acid, also known as Vitamin A acid.

The preparation is a formulation of tretinoin suitable for local or topical administration. The term "topical" means a compound of tretinoin incorporated in a suitable pharmaceutical carrier which may be applied at the growth site of the nail for local action.

The topical composition may comprise tretinoin formula fed with dimethylacetamide, ethyl alcohol, propylene glycol or combinations thereof.

Typical local preparations include those pharmaceutical forms in which the compound is applied externally by direct contact with the surface to be treated. Conventional pharmaceutical forms for this purpose include ointments, waxes, lotions, pastes, jellies, spray, aerosols and the like in aqueous or non-aqueous formulations. The term "ointment" refers to formulations including creams which are oleaginous, absorbative, and water soluble, and include emulsion type bases such as petrolatum, lanolin, polyethylene glycols as well as mixtures thereof.

The percentage by weight of tretinoin in the preparation can vary between about 0.025 and 50% of the entire pharmaceutical preparation, preferably from about 0.025 to about 5%. In the preparation, the pharmaceutical carrier for the active constituent in the topical application represents the remaining amount of the composition.

The preparation of topical compositions is well known and, for example, disclosed in U.S. Pat. Nos. 4,139,619 and 4,596,812.

The preparation contained tretinoin can be administered by spraying, dabbing, swabbing or other manner of application of the preparation on the region of the nail where it emerges from the skin, such as the proximal nail fold in humans. Other less specific methods can be employed provided the active ingredient tretinoin is delivered to the growth region of the nail.

As explained, the tretinoin-containing composition is periodically applied to the growth area of the nail in a suitable regimen to achieve nail growth. In animals, it may be necessary to apply the formulation with greater frequency in order to compensate for loss due to activity of the animal. In order to simplify the topical application of the preparation in humans, its use can also be effected by nail polishes, moistened pads or immersion of the nails in liquid solutions.

The treatment of the invention is not only suitable for correction of deficiencies in the nails, but also to achieve a growth greater than normal when so desired.

Although the invention has been described in relation to a specific embodiment thereof, numerous modifications and variations can be made within the scope and spirit of the invention as defined in the attached claims.

What is claimed is:

1. A method of treating nail units of animals including humans comprising topically applying to the nail unit of an animal a preparation comprising tretinoin to promote growth of the nail unit, the tretinoin being present in said preparation in an amount between 0.025 and 50% by weight.

2. A method as claimed in claim 1 wherein the application is applied to the nail unit a number of times over a period of time.

3. A method as claimed in claim 1 comprising formulating into said preparation in addition to the tretinoin, dimethylacetamide, ethyl alcohol, propylene glycol or combinations thereof.

* * * * *